US006692790B2

United States Patent
Liu et al.

(10) Patent No.: US 6,692,790 B2
(45) Date of Patent: Feb. 17, 2004

(54) PROTEINACEOUS COATING

(75) Inventors: Yuelian Liu, Utrecht (NL); Klaas de Groot, Heemstede (NL); Pierre Jean F. Layrolle, Utrecht (NL)

(73) Assignee: Chienna B.V., Bilthoven (NL)

( * ) Notice: Subject to any disclaimer, the term of this patent is extended or adjusted under 35 U.S.C. 154(b) by 0 days.

(21) Appl. No.: 10/212,468

(22) Filed: Aug. 5, 2002

(65) Prior Publication Data

US 2003/0113438 A1 Jun. 19, 2003

Related U.S. Application Data

(63) Continuation of application No. PCT/NL01/00071, filed on Feb. 1, 2001.

(30) Foreign Application Priority Data

Feb. 4, 2000 (EP) ............................................. 00200393

(51) Int. Cl.[7] .................... A61L 27/00; A61L 27/14; A61L 27/28; A61L 27/54; B05D 1/18
(52) U.S. Cl. ................. 427/2.26; 427/2.1; 427/2.24; 427/2.27; 427/243; 427/270; 427/283; 427/336; 427/338; 427/403; 427/414; 427/430.1

(58) Field of Search ............................... 427/2.1, 2.24, 427/2.26, 2.27, 243, 270, 283, 336, 338, 403, 414, 430.1

(56) References Cited

U.S. PATENT DOCUMENTS 4,713,076 A 12/1987 Draenert
6,569,489 B1 * 5/2003 Li ............................ 427/2.26

FOREIGN PATENT DOCUMENTS

| EP | 0 806 212 | 11/1997 |
|---|---|---|
| EP | 98203085.0 | 9/1998 |
| WO | WO 97/41273 | 11/1997 |

* cited by examiner

Primary Examiner—Shrive P. Beck
Assistant Examiner—Jennifer Kolb Michener
(74) Attorney, Agent, or Firm—Banner & Witcoff, Ltd.

(57) ABSTRACT

The invention relates to a method for providing a proteinaceous coating on a medical implant, comprising the steps of: submersing the implant in a first aqueous solution comprising a protein and magnesium, calcium and phosphate ions through which a gaseous weak acid is passed; degassing the solution; allowing a coating to precipitate onto the implant; submersing the coated implant in a second solution to redissolve the magnesium, calcium and phosphate ions and to obtain the proteinaceous coating.

24 Claims, 3 Drawing Sheets

Ca-P/BSA coating

Figure 2A:
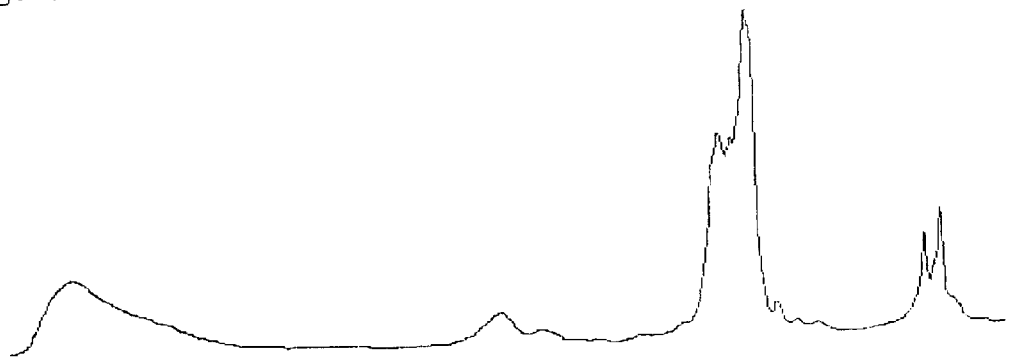

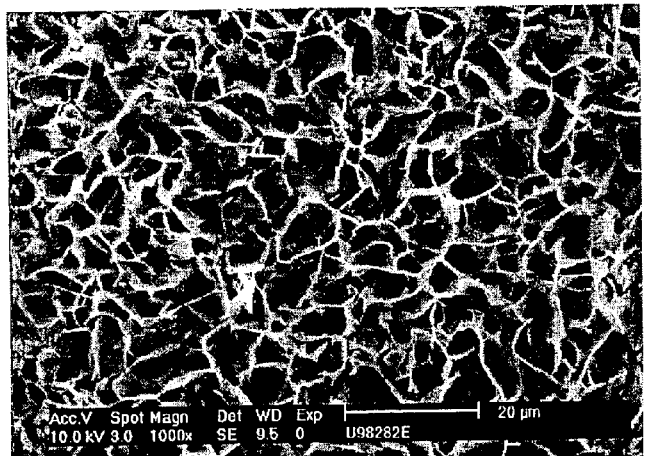
Fig 1a: Ca-P/BSA coating
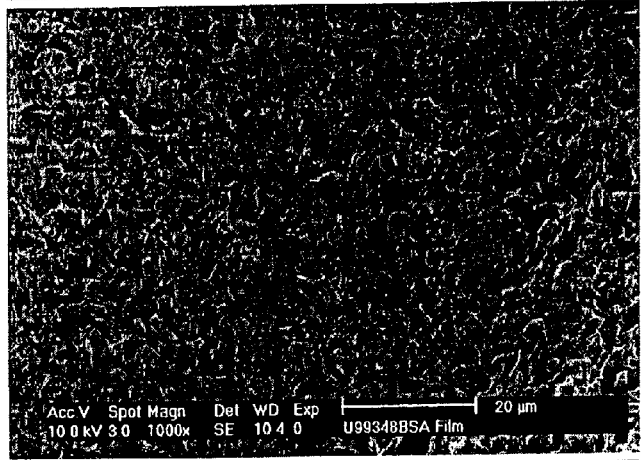
Fig 1b: "demineralized"
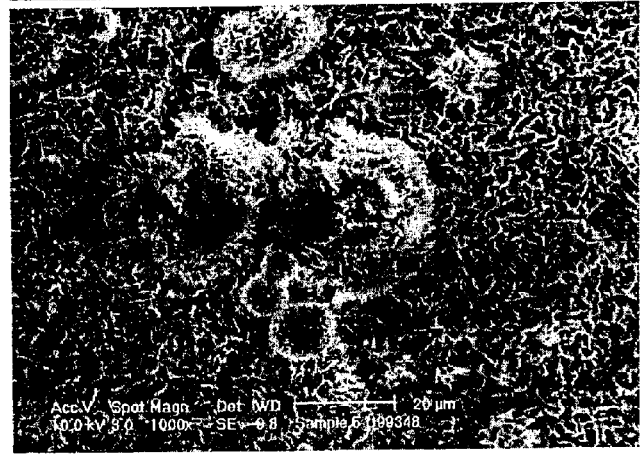
Fig. 1c: "remineralized"

Figure 3: EDS of remineralized protein matrix
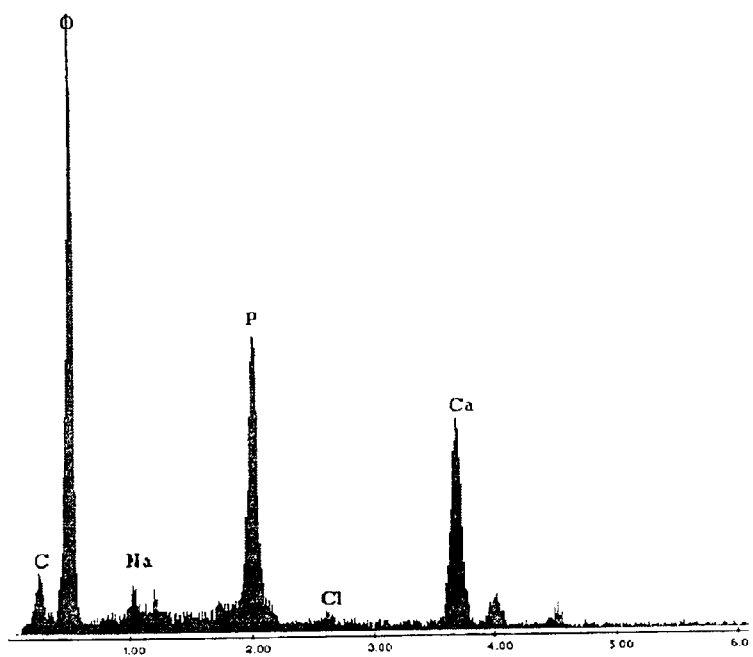

PROTEINACEOUS COATING

This application is a continuation of prior application no. PCT/NL01/00071, filed on Feb. 1, 2001; which claims priority from European Patent Application No. EP 00200393.7, filed on Feb. 4, 2000.

The invention relates to the field of medical implants. More in particular, the invention relates to a coating which improved the biocompatibility and bone-bonding properties of medical implants, such as orthopedic and dental prostheses.

Recently, a biomimetic coating has been developed for coating medical implants with ceramic materials, such as bone-like hydroxyapatite. This technology has been disclosed in European patent application 98203085.0 and comprises soaking an implant material, e.g. a scaffold for tissue engineering bone, into a super saturated calcium phosphate solution resembling a physiological fluid. A calcium phosphate layer uniformly precipitates on the implant surface under modulated nucleation and crystal growth conditions. This method mimics the way hydroxyapatite bone crystals are formed in the body. Considering the physiological conditions under which the biomimetic coating is grown from a fluid at body temperature, biologically active agents, such as antibiotics, can be coprecipitated.

In EP 0 806 212, an implantable coated device is disclosed that comprises a calcium phosphate layer, in which a biologically active substance may be incorporated. The coating comprising calcium phosphate and a growth factor can give rise to an enhancement of bone formation. For the preparation of the coating the surface of the device needs to have a roughness(Ra value) 10–1,000 nm.

WO 97/41273 describes a process for coating a metallic or ceramic substrate by heating a certain mineral solution, in which the substrate is immersed, to a high temperature until the pH is at least 8, after which deposition of crystalline carbonated hydroxyappetite is on the substrate is induced. Such a coating is reported to be osteoinductive, but the incorporation of bioactive agents is not disclosed. It is unlikely that the process would be suitable for such purpose, since the combination of a high temperature and a high pH, would have a detrimental effect on the thermosensitive bioactive agents.

Many mineralized tissues in living organisms are composed of crystals formed under well-controlled conditions. Proteins are key participants in the control process. Some proteins envelop the individual crystals, whereas others are occluded inside the crystals. How these proteins become occluded inside a crystal and what their role is in the crystallization process and in the determination of the properties of the crystal still remains unclear.

The present invention seeks to find a way of using the expected controlling function of proteins in mineralization processes. In particular, it is an object of the invention to find a way of using a protein to induce mineralization, calcification and/or the formation of bone tissue on a medical implant.

These objects, as well as other objects of the invention that will become clear from the present description, have been achieved by virtue of a proteinaceous coating to the implant which is applied thereto in a specific manner. Accordingly, the invention relates specifically to a method for providing a proteinaceous coating on a medical implant, comprising the steps of:

submersing the implant in a first aqueous solution comprising a protein and magnesium, calcium and phosphate ions through which a gaseous weak acid is passed;

degassing the solution;

allowing a coating to precipitate onto the implant;

submersing the coated implant in a second solution to redissolve the magnesium, calcium and phosphate ions and to obtain the proteinaceous coating.

Surprisingly, it has been found that a proteinaceous coating may be provided on a medical implant, which coating induces nucleation and growth of calcium phosphate crystals, both in vitro and in vivo. Although the coating itself will typically not contain any calcium phosphate material, it has been found to act as a type of template or matrix for mineralization. This advantageous property allows for the application of the medical implant to serve as a scaffold for tissue engineering bone tissue.

On the other hand, said property of course also increases the suitability of the implant for the purpose it originally had, i.e. being implanted in a patient in need of a bone substitute. The proteinaceous coating described herein can induce deposition of a variety of calcium phosphate compounds containing carbonate and others ions on the surface of an implantable device. The layers will be similar in composition and crystallinity with bone and teeth minerals and have desired bioresorbability, bone-bonding properties to improve the biological fixation of medical devices to living calcified tissue.

The proteinaceous coating may further form a composite with calcium phosphate crystals, for instance in vivo, leading to a biomimetic coating with mechanical properties superior to those of conventional ceramic coatings. It is believed that the protein may function as a reinforcement of a biomimetic coating by bonding calcium phosphate crystals together.

Furthermore, the proteinaceous coating enhances attachment of cells and improves the biocompatibility and bone-bonding properties of medical implants.

The medical implant on which a coating is applied in accordance with the invention may be of any inorganic, metallic, polymeric or organic material. The implant may be flat, dense or of a complex shape. It may have a porous, beaded or meshed ingrowth surface.

Metals, such as stainless steel, titanium, nickel, cobalt, chrome, niobium, molybdenum, zirconium, tantalum, and combinations thereof, can be coated for orthopaedic and dental applications. For example, devices used in total hip arthroplasty such as porous or non-porous acetabular cups and the proximal region of hip stems may be coated.

Ceramic materials, such as alumina and zirconia, glasses such as bioactive glasses made of $CaO$—$SiO_2$—$P_2O_5$, and calcium phosphates, such as hydroxyapatite and tricalcium phosphate, may be coated.

The subject coatings can be applied to various polymers and plastics, more preferably biocompatible or bioresorbable ones like polyactive™, a copolymer of polyethylene glycol and polybutylene terephtalate.

Before applying the coating, the substrates are preferably cleaned or treated to remove any surface contaminants and to promote good adhesion of the coating. Various methods for cleaning may be employed. The metallic implants may be rinsed with a degreaser, i.e. acetone, alkyl alcohols, etc. and then thoroughly rinsed with pure water.

In order to improve coating adhesion, various surface treatments may be applied to metal implants. Mechanical surface treatments, such as sand-blasting, scoring, polishing and grinding can increase surface roughness of the implants and improve the bonding strength between the coatings and substrate. For similar purposes, chemical surface treatments may be also applied to metal substrates prior to coating.

Among others chemical treatments available for metals, acid etchings will be preferred by treating implantable devices with strong mineral acids, such as hydrofluoric, hydrochloric, sulfuric, nitric and perchloric acids. It may also useful to treat the metal devices with oxiding agents such as nitric acid, peroxyhalogen acids, hydroxyperoxides, or hydrogen peroxide to form a fresh metal oxide layer. After the mechanical or chemical treatment, it is necessary to rinse the implants with pure water under ultrasounds for removal of surface contaminants.

The method for coating medical implants consists of soaking medical implants into a calcifying solution comprising a protein at low temperature. This simple method is based on the finding that calcium phosphates are more soluble in mildly acidic medium than at neutral and even basic pH. This also applies at conditions which essentially do not affect the stability and activity of the protein in a harmful way. Thus, aqueous solutions of calcium and phosphate ions and a protein can be more concentrated at mildly acid than at neutral pH. In other words, calcium phosphates precipitate at neutral or basic pH while they remain soluble at mildly acidic pH from a solution having the same concentrations of salts.

An increase of pH in the solution can induce the following stages: under-saturation, super-saturation or the formation of a meta-stable state, nucleation and crystal growth. Calcium phosphate nuclei can form onto a substrate—heterogeneous nucleation—when a solution has reached the super-saturation limit or the meta-stable state. At the super-saturation state, crystals can subsequently grow from meta-stable fluids. At higher saturation, homogeneous nucleation or precipitation in the solution is the predominant process. This invention makes use of pH changes to control the above stages and to induce the deposition of carbonated calcium phosphate layers on the surface of medical implants.

The above object can be achieved by bubbling a gaseous weak acid, preferably carbon dioxide gas, into a calcifying solution in order to decrease pH and thereby to increase the solubility of calcium phosphate salts. It is well known that natural sparkling water has a mildly acidic pH resulting from dissolved carbon dioxide gas. It is also an important feature that the pH of mineral water slowly increases to neutral or slightly basic pH during the natural release or exchange of dissolved carbon dioxide gas with air.

In a number of preferred embodiments, the bubbling of carbon dioxide gas into the calcifying solution is required. Carbon dioxide gas will dissolve in the calcifying solution and form hydrogen carbonate ions in water. The said medical implants are placed into an aqueous calcifying solution in which a gaseous weak acid, such as carbon dioxide gas, is passed through to produce a weakly acidic media. The initial pH of said calcifying solution is maintained in the range 3–7, preferably about 5.5 to 6.5 by bubbling $CO_2$ gas. The carbon dioxide gas is introduced into the solution at a sufficient pressure to continuously generate bubbles. The pressure of $CO_2$ gas will be in the range 0.1–10 bars, preferably within 0.5 to 1.5 bars, more preferably about 1 bar.

In a method according to the invention, the presence of magnesium, calcium and phosphate ions in the calcifying solution is essential. Particularly, the presence of magnesium has been found to be important for controlling the crystal growth of the coating during deposition from the calcifying solution. An optimum control of crystal growth leads to a uniform, strong and wear resistant coating. Particularly, the attachment of the coating to the substrate is beneficially effected by the presence of magnesium ions in the calcifying solution. A coating prepared according to the invention, preferably has crystals having a size in the submicrometer range. In a preferred embodiment, additional inhibitors of crystal growth, such as carbonate ions, may be incorporated in the calcifying solutions. If required, counter ions, like sodium and chloride might also be present to provide a constant ionic strength.

Preferably, the calcifying solution is prepared while the gaseous weak acid is bubbled through, in order to avoid precipitation. The introduction of the gas decreases the pH of the solution and allows the complete dissolution of the magnesium, calcium and phosphate, and possible other salts. Preferably, the bubbling is started at least 5 minutes before, and during, the addition of the salts. Thus, the pH is lowered to approximately 3–8, more preferably to 5.5–6.

Of course it is also possible to start the bubbling with the gaseous weak acid after the addition of the desired amounts of the salts to the solution. Once the bubbling is started, in accordance with this embodiment, it is important to ensure that the salts dissolve completely.

The calcifying solution is preferably prepared with ultra pure water and pure grade chemicals. The calcifying solution is preferably filter sterilized through a 0.2 microns filter membrane prior to use. The molar calcium to phosphorus ratio in the calcifying solution is generally within the range 1–3, more preferably between 1.5 to 2.5. The concentrations of the ions in the calcifying solution are chosen such, that in the absence of the gaseous weak acid, the solution is super-saturated or oversaturated. The molarity of the calcium source will generally be in the range 0.5–50 mM, preferably about 2.5 to 25 mM. The phosphate source will generally be from about 0.5 to 20 mM, more preferably about 1 to 10 mM. The concentration of magnesium in the calcifying solutions will usually be within the range 0.1–20 mM, more preferably about 1.5 to 10 mM. The carbonate concentration will range from 0 to 50 mM, more preferably 0 to 42 mM. The ionic strength will be within the range 0.10–2 M, more preferably in between 0.15 to 1.5 M. The calcifying solution is preferably stirred to approximately 10–1000 rpm, more usually 50 to 200 rpm. The temperature is maintained at about 5–80° C., preferably in the range of about 5–50° C.

The protein is preferably present in the above described calcifying solution. It may be added before, during or after the dissolution of the various ions that are desired in the coating. The concentration in which the protein is preferably present in the calcifying solution preferably lies between 0.001 and 10 g/l, more preferably between 0.01 and 1 g/l.

In principle, the present method may be carried out using any type of protein. Preferred, highly suitable proteins are electronegatively charged at the pH at which precipitation occurs. It is further preferred that the solubility of the protein is at least 1 gram per liter water at neutral pH. In addition, it is considered advantageous if the protein possesses disulfide bridges in its structure. Examples of highly suitable proteins include albumin, casein, gelatin, lysosime, fibronectin, fibrin and chitosan. In principle, any protein based on amino acids which have an isoelectric point below 7 and are negatively charged may be used. Examples of such amino acids include alanine, aspartic acid, cysteine, glutamine, glycine, isoleucine, leucine, methionine, proline, phosphorine, serine and valine. Particularly preferred proteins are synthetic proteins, such as polylysine, polyalanine, and polycysteine. Biologically active proteins, such as growth factors (e.g. BMP, FGF, TGF), may also be advantageously used.

Optionally, the proteinaceous coating may be bound to the implant covalently by making use of a coupling or linking agent. This agent should be capable of reacting with OH groups on the implant surface and with amino groups of the protein. The covalent bond will ensure a good mechanical attachment of the proteinaceous coating to the implant. The coupling agent is preferably chosen from the group of isocyanates, cyanuric acid, titanium alkoxides ($Ti(OR)_4$), and silicon esters, such as $Si(OR)_2Cl_2$, wherein R represents an alkyl group of 1–4 carbon atoms. In order to obtain the covalent linkage, the coupling agent is simply added to the calcifying solution in an appropriate amount which will typically lie between 1 and 20 wt. %, based on the weight of the solution.

The carbon dioxide has a limited solubility in aqueous solutions. In contact with air, a carbonated aqueous solution is free of $CO_2$ or completely degassed within few hours depending on the surface of solution in contact with air. The complete exchange of dissolved $CO_2$ gas with atmosphere may be performed in approximately 8 to 48 hours, more preferably between 12 to 24 hours. The natural release of $CO_2$ gas causes the pH of the remaining solution to increase. In others words, saturation in the calcifying solution can increase until the precipitation of the bioactive layers, including calcium phosphate and protein, on the surface of implantable materials occurs. Optionally, air can be bubbled through the solution to degas or aerate the solution and accelerate the escape, release or exchange of the gaseous weak acid. The initial and final pH values as well as pH changes with time depend on the amount of carbonate and phosphate salts added to the calcifying solution. The buffering capability can be adjusted to a desired pH value by adding more or less of phosphate and carbonate salts. The pH can be maintained within the desired range by introducing carbon dioxide gas. In essence, the flow of carbon dioxide can be adjusted by using an electro or selenoid valve piloted by the controller. During the natural release of $CO_2$ gas out of the calcifying solution, the pH will increase to about 6–10, more preferably about 7.5 to 8.5 after soaking for 24 hours. The carbonated calcium phosphate layer comprising the protein will precipitate on the surface of implantable devices at a pH value of within about 6.5–7.5. The said precipitation on the surface of medical implants is related to a heterogeneous nucleation step. The carbonated calcium phosphate crystals might subsequently precipitate into the calcifying solution by a crystal growth process. In accordance with the invention, heterogeneous nucleation is favored by the energetic stabilization of nucleus on the substrate. The high density of nucleation ensures a uniform deposition of carbonated calcium phosphate crystals onto the surface of medical implants.

In a method according to the invention, it may be desired to control the pH and thereby the nucleation stage by bubbling $CO_2$ gas for various time. The bubbling time is usually comprised between a few seconds to minutes, preferably about 1 to 600 seconds. The introduction of carbon dioxide causes a decrease of pH while the pH of calcifying solution has a tendency to increase naturally without bubbling $CO_2$ gas. The increase of pH may be due to the natural exchange of $CO_2$ gas with atmosphere and the buffering capability of the calcification solution. By adjusting the time and flow of $CO_2$ gas introduced into the calcifying solution, the pH can oscillate around a value ranging from 6 to 9, more preferably the pH of the calcifying solution can be maintained between 6.5 to 7.5. This pH oscillation is correlated to the nucleation stage of carbonated calcium phosphate crystals on the surface of medical implants. A high density of nucleation is thereby provided and carbonated calcium phosphate crystals can nucleate and grow onto the surface of medical implants. Homogeneous layers comprising ceramic material and protein can uniformly deposit on the implant substrate. The total thickness of layers will preferably be within the range 0.5–100 microns, more likely 0.5 to 50 microns. While the layers are thin, usually below 5 microns, the coatings can diffract the natural light forming colored fringes ranging from blue to red colors. This diffraction of light is similar to the phenomenon that may be observed when a drop of oil is present on water. For higher thickness, the layers give a shiny gray or white coloration.

The thus obtained coating comprises both ceramic material and the protein. In accordance with the invention, the ceramic material is removed by dissolution in a second, solution to provide the objective proteinaceous coating. The conditions under which the dissolution is carried out are to be chosen such that the ceramic material substantially completely dissolves and the protein substantially completely remains coated on the surface of the medical implant. In other words, care should be taken that hydrolyzation of the protein is avoided as much as possible. Although it may be expected that a (partial) denaturation of the protein takes place during this step, this is considered not to harm the inductive properties of the coating, and may in fact even be beneficial.

The dissolution may be accomplished by using an acidic solution, such as an aqueous solution of which the pH is preferably chosen in the range of from 2 to 5, more preferably from 3 to 4. The acid used for obtaining the objective pH can in principle be any acid suitable for attaining the desired degree of acidity. Suitable acids do not adversely affect the protein. Examples are hydrogen phtalate and hydrochloric acid, which acids are preferably used in aqueous solutions of 30–70 mM.

In an other embodiment the dissolution of the ceramic material is accomplished in a solution comprising a complexing or sequestering agent to redissolve the magnesium, calcium and phosphate ions and to obtain the proteinaceous coating. The solution comprising the sequestering agent is preferably an aqueous solution of which the pH may be alkaline, neutral or acidic. The pH is preferably in the range of 2–9, more preferably in the range of 2–7 and. Most preferably the pH is in the range of 4–6, because of the better solubility of free calcium and magnesium at an acidic pH, in combination with a relatively high degree of complexation.

In principle any sequestering agent for calcium and magnesium can be used to dissolve the mineral part of the coating. A suitable sequestering agent does not adversely affect the protein. The sequestering agent may be used alone or together with one or more other sequestering agents, e.g. to optimize the complexation of the different cations in the ceramic materials.

Very good results have been achieved with ethylene diamine tetra acetate (EDTA, e.g. the sodium salt)as a sequestering agent. A highly preferred pH for this particular embodiment is in the range of 4–6.

It has been found that ceramic material can be dissolved from the coating by using a sequestering agent in a wide concentration range. A sequestering agent may be used in any concentration, up to its saturated concentration. Preferably the concentration is between 0.1 and 20 wt. %, more preferably between 1 and 10%.

Dissolution of the ceramic material by using a sequestering or complexing agent can be performed such that the protein does not significantly denaturate, which can be advantageous for particular applications.

Once the ceramic material has essentially completely been removed, the medical implant with the proteinaceous coating may be taken out of the solution in which the ceramic material has been dissolved and optionally rinsed with water or demineralized water in order to remove trace amounts of acid and/or ceramic material. The medical implant thus obtained has been found to induce mineralization, calcifications and/or formation of bone tissue in vitro and in vivo. Accordingly, the implant has an improved performance as a bone substitute in comparison with the implant without the proteinaceous coating.

It has also been found that upon exposure to a calcifying solution, recalcification of the protenaceous layer may take place in such a way that the morphology of the layer after remineralization closely resembles that of the intermediate coating, comprising protein and calcium phosphate, before the decalcification. This recalcification process is expected to take place in vivo, depending on the site of implantation. Since the layer may completely resorb the minerals, the risk for creating brittle zones in the coatings that may cause fracture, is minimized.

Furthermore, the inductive property of the coating makes the coated implant highly suitable for use as a scaffold for tissue engineering bone. In this application, cells may be seed onto the implant and cultured to form or to start forming bone tissue.

The invention will now be elucidated by the following, non-restrictive examples.

EXAMPLE

Materials and Methods

Materials

High-grade titanium alloy (Ti6Al4V) plates of 20×20×1 mm were used. The calcifying solutions were prepared with reagent pure chemicals (Merck) and demineralized water. The protein used for this study was bovine serum albumin (BSA) in a powder form (fraction V, >98%, Sigma). BSA is a single polypeptide chain consisting of about 583 amino acid residues (M.W. 66,4303). At pH 5–7, it contains 17 intra-chain disulfide bridges and 1 sulfhydryl group (Sigma A-8806)

Methods

Preparation of Biomimetic Calcium Phosphate Coatings

Ti6Al4V plates were ultrasonically cleaned for 15 min in acetone, then ethanol (70%) and finally demineralized water. All the samples were etched with a mixture of hydrofluoric acid (HF, 40 wt. %) nitric acid ($HNO_3$, 65 wt. %) and demineralized water for 10 min under ultrasounds. After etching, they were thoroughly rinsed with demineralized water.

Two layers of calcium phosphate were subsequently applied on the Ti6Al4V samples by using a biomimetic method. The first layer was prepared at high nucleation conditions in the presence of inhibitors of crystal growth under a concentrated Simulated Body Fluid (SBF×5) (Table 1). A calcifying solution was made by dissolving NaCl, $CaCl_2.2H_2O$, $MgCl_2.6H_2O$, $NaHCO_3$ and $Na_2HPO_4.2H_2O$ salts in 1000 ml of demineralized water and passing through carbon dioxide gas. After immersion for 24 hours at 37° C., pH of this solution has increased from 5–6 till 8. The plates were carefully rinsed with demineralized water for 10 minutes and finally dried at room temperature overnight. A thin, dense and amorphous calcium phosphate layer was uniformly deposited on the titanium alloy surface. This thin layer diffracted natural light forming colorful fringes and was so-called Rainbow coating. The Rainbow coated Ti6Al4V plates were used as seed surface for growing a subsequent crystalline apatitelayer.

TABLE 1

| Solution | Buffer | Ionic concentration (mM) | | | | | | | |
| --- | --- | --- | --- | --- | --- | --- | --- | --- | --- |
| | | $Na^+$ | $K^+$ | $Mg^{2+}$ | $Ca^{2+}$ | $Cl^-$ | $HPO_4^{2-}$ | $SO_4^{2-}$ | $HCO_3^{2-}$ |
| HBP | — | 142.0 | 5.0 | 1.5 | 2,5 | 147.8 | 1.0 | 0.5 | 4.0 |
| SBF ×5 | $CO_2$ | 733.5 | — | 7.5 | 12.5 | 739.0 | 5.0 | 2.0 | 21.0 |
| CPS | Tris-HCl | 140.0 | — | — | 4.0 | 144.0 | 2.0 | — | — |
| SPS | KHphtalate-HCL | 137.0 | — | — | — | 177.0 | — | — | — |

The second layer was prepared under conditions conducive to crystal growth, namely, by immersing Ti6Al4V implants in supersaturated calcium phosphate (CPS, Table 1) solution for 48 hours at ambient temperature. These solutions also contained bovine serum albumin (Bovine serum albumin (BSA) in a powder form, fraction V, >98%, Sigma) at concentrations of 0, 0.01, 0.1 and 1 mg/ml BSA.

Samples were then washed in demineralized water and air-dried at ambient temperature. Scanning Electronic Microscope (SEM, Philips, Model 525, 15 kV, carbon sputtered samples) revealed the protein films to be leaf-like structures, repeating the original lamellar hydroxyapatite crystals (FIG. 1a). During this coating process, a thick (30–50 $\mu$m) and dense crystallized apatite film was deposited uniformly upon the surface of the substrate. The "Rainbow" layer acts as a seed structure and is resorbed during this step.

Treatment of these coated implants with acidic solutions (SPS, Table 1) at 37° C. led to the complete dissolution of crystallized mineral components (calcium and phosphate) (13), a fine (7–10 $\mu$m), soft and porous (FIG. 1b) protein matrix being left behind.

Scanning electron microscopy revealed the remineralization process to have converted the protein layer back to the original lamellar film morphology. Some overgrowth of rose-like crystals clusters was also seen on top of the films (FIG. 1c). Implants devoid of a protein film did not become coated with a mineralized layer.

Figure 2B:
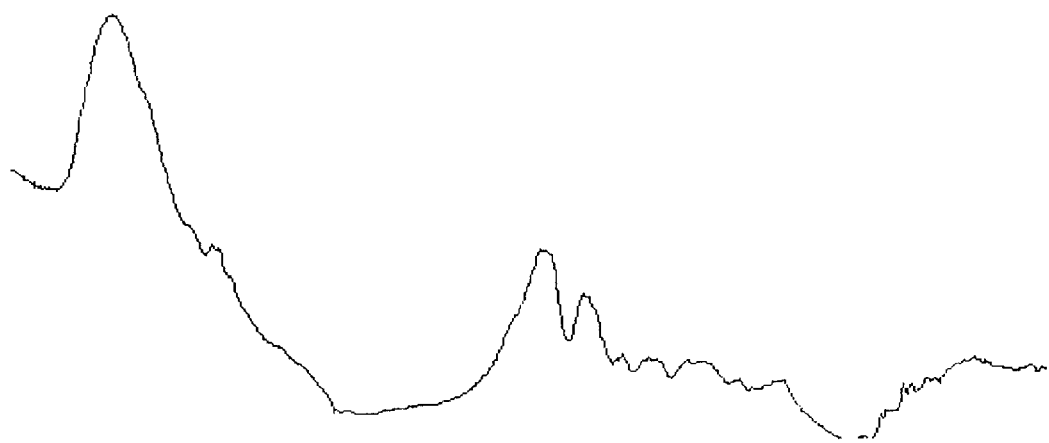
Figure 2C:

Fourier Transform InfraRed spectrometry (FT-IR, Perkin-Elmer, Spectrum 1000) using transparent KBr pellets) of the original mineralized film clearly shows the characteristic phosphate doublet at 563 and 602 $cm^{-1}$ (FIG. 2a). This doublet absent after demineralization (FIG. 2b). The phosphate doublet re-appears after remineralization (FIG. 2c). The BSA shows a large peak due to OH, >NH and absorbed water around 3500 $cm^{-1}$ and characteristic bands of >C=O and —$COO^-$ at 1640 $cm^{-1}$ and 1550 $cm^{-1}$.

The protein films were insoluble in solution of both acidic and neutral pH. After release of coating, thickness of BSA film was measured by using a magnetic induction probe (Electrophysik Minitest 2100). The measuring range of this apparatus is between 0 and 100 microns. The measurements were repeated 10 times and averages were obtained on each sample Their thickness increased as the concentration of BSA in the bathing SCP solution was raised (Table 2).

TABLE 2

Properties of the protein film for various protein concentrations in mineralization solution

| Concentrations of BSA in coating solution (mg/ml) | Thickness of the re-mineralized coating (μm) (SD) | Thickness of the protein film (μm) (SD) | Pore size (Ø) of the protein film (μm) (SD) |
|---|---|---|---|
| 0.01 | 34.52 (5.5) | 6.72 (1.67) | 9.07 (1.30) |
| 0.1 | 38.75 (7.32) | 7.80 (1.72) | 2.67 (1.08) |
| 1.0 | 37.25 (7.70) | 10.00 (1.06) | 1.07 (0.25) |

The pores between the crystals remain as pores in the demineralized protein film (Table 2). Crystal size—and hence pore size—decreased as the concentration of BSA in the SCP solution was elevated. The thickness of the demineralized protein film increased from about 20% to 27% of the precursor mineralized film with increasing BSA concentration. No residual apatite crystals were seen in these protein films.

Energy dispersive x-ray analysis (EDS, Voyager) gave evidence of residual calcium and phosphate in the protein films being below 1.14% (Table 3).

TABLE 3

EDS comparison if atomic percentage by element in coated implants

| Atomic % | C | O | Na | P | Cl | Ca | Ca/P |
|---|---|---|---|---|---|---|---|
| Apatite/BSA coating | 35.28 | 40.75 | — | 10.22 | 0.47 | 13.28 | 1.3 |
| "demineralized" protein matrix | 35.35 | 24.81 | 3.2 | 1.14 | 0.96 | 0.96 | 0.8 |
| "re-mineralized" protein matrix | 33.32 | 46.83 | 1.68 | 8.55 | 0.78 | 8.38 | 1.0 |

When implants that were covered with these protein films were again immersed in SCP solutions (without BSA) under the same conditions, they became recoated with a thick (30 μm), dense layer of apatite (deducted from results shown in FIG. 3).

What is claimed is:

1. A method for providing a proteinaceous coating on a medical implant, comprising the steps of:
   submersing the implant in a first aqueous solution comprising a protein and magnesium, calcium and phosphate ions through which a gaseous weak acid is passed;
   degassing the solution;
   allowing a coating to precipitate onto the implant;
   submersing the coated implant in a second solution to substantially remove the magnesium, calcium and phosphate ions from the implant and to obtain the proteinaceous coating.

2. A method according to claim 1, wherein the gaseous weak acid is carbon dioxide.

3. A method according to claim 1, wherein the implant is a metallic, organic, polymeric, or ceramic implant.

4. A method according to claim 1, wherein the calcium and phosphate ions are present in the first solution in a molar ratio of between 1 and 3.

5. A method according to claim 1, wherein the calcium and phosphate ions are present in the first solution in a molar ratio of between 1.5 and 2.5.

6. A method according to claim 4, wherein the first solution comprises 0.5–50 mM, preferably 2.5–25 mM, calcium ions, and 0.5–20 mM, preferably 1–10 mM phosphate ions.

7. A method according to claim 1, wherein the first solution comprises 0.1–20 mM magnesium ions.

8. A method according to claim 1, wherein the first solution comprises 1.5–10 mM magnesium ions.

9. A method according to claim 1, wherein the first solution further comprises 0–50 mM carbonate ions.

10. A method according to claim 1, wherein the first solution further comprises 0–42 mM carbonate ions.

11. A method according to claim 1, wherein the ionic strength of the first solution is in the range of 0.1–2 M.

12. A method according to claim 1, wherein the ionic strength of the first solution is in the range of 0.15–1.5 M.

13. A method according to claim 1, wherein the pressure of the gaseous weak acid is in the range of 0.1–10 bar.

14. A method according to claim 1, wherein the pressure of the gaseous weak acid is in the range of 0.5–1.5 bar.

15. A method according to claim 1, wherein the temperature of the first and second solutions are independently chosen in the range of 5 to 80° C.

16. A method according to claim 1, wherein the temperature of the first and second solutions are independently chosen in the range of 5 to 50° C.

17. A method according to claim 1, wherein the protein is chosen from the group of albumin, casein, gelatin, lysosime, fibronectin, fibrin, chitosan, polylysine, polyalanine, polycysteine, growth factors, and combinations thereof.

18. A method according to claim 1, wherein the protein is present in the first solution in a concentration of between 0.001 and 10 g/l.

19. A method according to claim 1, wherein the second solution is an aqueous acidic solution.

20. A method according to claim 19, wherein the second solution has a pH of between 2 and 5.

21. A method according to claim 1, wherein the second solution comprises a sequestering or complexing agent.

22. A method according to claim 21, wherein the sequestering or complexing agent is ethylene diamine tetra acetate.

23. A method according to claim 21, wherein the sequestering agent is present in a concentration between 0.1 and 20 wt. %.

24. The method of claim 1 wherein the proteinaceous coating induces mineralization and/or formation of bone tissue.

* * * * *